Figure 1:
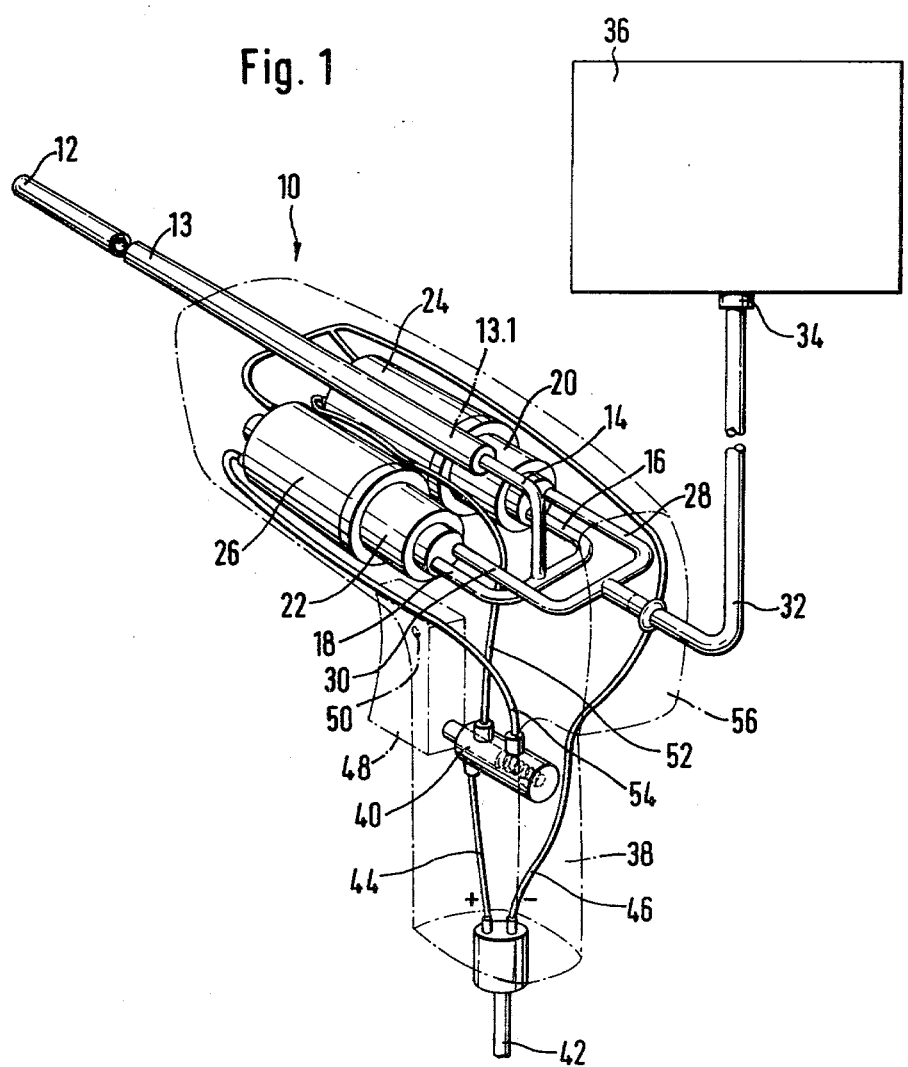

United States Patent [19]

Du Toit

[11] 4,282,867
[45] Aug. 11, 1981

[54] CLEANING FLUID INJECTION DEVICE

[75] Inventor: Rudolph M. Du Toit, Paarl, South Africa

[73] Assignees: Christopher Edward; Hans Rudolf Kabutz; Frank Corker, all of South Africa

[21] Appl. No.: 100,518

[22] Filed: Dec. 5, 1979

[51] Int. Cl.³ .............................................. A61H 9/00
[52] U.S. Cl. ..................................... 128/66; 128/230; 128/248
[58] Field of Search .................. 128/230, 251, 66, 248

[56] References Cited

U.S. PATENT DOCUMENTS

| | | | |
|---|---|---|---|
| 3,731,676 | 5/1973 | Rebold | 128/230 |
| 3,783,867 | 1/1974 | Summersby et al. | 128/230 |
| 3,794,031 | 2/1974 | Bloom | 128/251 |

*Primary Examiner*—John D. Yasko
*Attorney, Agent, or Firm*—Pearne, Gordon, Sessions, McCoy & Granger

[57] ABSTRACT

A portable medical treatment device is provided which includes an injection nozzle shaped and dimensioned to enter a human body cavity. At least one pump is provided having a suction connection connectable to a cleaning fluid reservoir and having a delivery connection connected via a delivery conduit to the nozzle. By means of drive means the pump is driven during use in order to pump cleaning fluid under pressure from the reservoir to the nozzle.

3 Claims, 2 Drawing Figures

CLEANING FLUID INJECTION DEVICE

This invention relates to a portable medical treatment device for injecting cleaning fluid into a cavity to be cleaned such as, for example, an ear cavity or a wound.

According to the invention, there is provided a portable medical treatment device which includes an injection nozzle shaped and dimensioned to enter a human body cavity; at least one pump having a suction connection connectable to a cleaning fluid reservoir and having a delivery connection connected via a delivery conduit to the nozzle; and drive means for driving the pump during use in order to pump cleaning fluid under pressure from the reservoir to the nozzle.

The pump may be in the form of a positive displacement pump and the drive means may include an electric motor drivingly connected to the pump. The electric motor may be of a kind which is energisable from a low voltage source such as a battery or low voltage transformer.

The device may have a generally pistol-shaped appearance and may include a handle shaped like a pistol grip and may include a trigger like switch in the handle.

The device may be provided with two pumps, the pumps having their delivery conduits connected in parallel to the injection nozzle.

The device may further include a cleaning fluid reservoir, and a suction conduit inter-connecting the pump suction connection with the reservoir. The reservoir may be remote from the pump and the suction conduit inter-connecting the pump suction connection and the reservoir may be flexible.

The invention will now be described by way of example with reference to the accompanying diagrammatic drawings.

In the drawings, there is shown in

Figure 2:
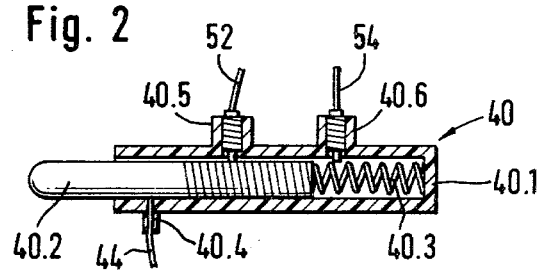

FIG. 1 a device according to the invention in three dimensional view with a cut-away section through its body and handle; and FIG. 2 a cross-sectional side view of a switch for the device according to the invention.

Referring to the drawings, a device 10 in accordance with the invention comprises an injection nozzle 12 for injecting cleaning fluid under pressure into a cavity such as an ear cavity. The nozzle 12 is provided at the end of a cylindrical tube 13 which is connected by a conduit 14 to the delivery conduits 16 and 18 of pumps 20 and 22 respectively. The pumps 20 and 22 are drivingly connected to electric motors 24 and 26 respectively.

The suction connections 28 and 30 of pumps 20 and 22 are connected tby means of a flexible tube 32 to the outlet 34 of a cleaning fluid reservoir 36.

The device 10 has a handle in the form of a pistol-like grip 38, and the cylindrical tube 13 extending like a pistol barrel with respect to the grip 38. The motors 24 and 26 and the pumps 20 and 22 are positioned above a switch 40, with the cylindrical tube 13 positioned above the motors 24 and 26 and pumps 20 and 22. The switch 40 is provided in the grip 38.

The pumps 20 and 22 are preferably vane pumps.

The end 13.1 of tube 13 remote from the nozzle 12 is connected via conduit 14 to the delivery conduits 16 and 18 of pumps 20 and 22.

The motors 24 and 26 are energisable from a low voltage direct current source 42 via leads 44 and 46 and via switch 40 operable trigger fashion by button 48 pivotally connected at 50 to the grip 38.

The switch 40 has a housing 40.1, a piston member 40.2, a compression spring 40.3, a contact point 40.4 connected to lead 44, and two contact points 40.5 and 40.6 connected to motors 24 and 26 via leads 52 and 54.

The device 10 is enclosed in a suitable housing 56 such as a housing moulded from synthetic rigid plastics material.

In use, the reservoir 36 is filled with a cleaning fluid and preferably placed at a higher elevation than the standard working level of an operator using the injection device 10, thereby providing fluid at a positive head to the pumps 20 and 22. The operator holds the device 10 by the grip 38.

To clean out a cavity such as an ear cavity, the nozzle 12 is carefully inserted down such cavity, and once in position, the trigger 48 is initially pulled only to such an extent as to energise motor 24. This results in pump 20 coming into operation and consequently pumping of cleaning fluid from the reservoir 36 to the nozzle 12 and from the nozzle into the ear cavity takes place.

Should a greater volume of cleaning fluid be desired, then the trigger 48 can be pulled even further so as to energise motor 26 and consequently activate pump 22 as well.

The cylindrical tube 13 like the nozzle 12, is dimensioned to enter a human body orifice.

If desired, replaceable nozzles of different shapes may be provided for different cavities. Thus, a nozzle for washing an open wound may have a shape which is different from that needed for washing an ear cavity.

The device has the advantage that it can be transported by a medical practitioner from place to place and is even available for use in a patient's home.

I claim:

1. A portable medical treatment device for irrigating the human ear canal comprising:
   (a) a cylindrical tube having a cleansing fluid passage and being dimensioned to enter an aural passage of a human body;
   (b) an injection nozzle provided at one end of the tube and constituting an outlet from the fluid passage;
   (c) at least two pumps connected in parallel, each having a suction side connection to a cleansing fluid reservoir and a delivery side for connection to the passage;
   (d) at least a pair of electrical motors adapted to each drive a respective one of the pumps for pumping cleansing fluid under pressure from the reservoir to the nozzle via the cleansing fluid passage; and
   (e) electrical control means adapted to sequentially energize one or both of the motors to vary the cleansing fluid output from the injection nozzle.

2. A device as claimed in claim 1, in which the pumps are in the form of positive displacement pumps, and in which the electrical motors are drivingly connected to the pumps.

3. A device as claimed in claim 1, including a housing of generally pistol-shaped appearance with a handle shaped like a pistol grip, the handle including a push button type electrical switch, the pump being provided above the switch and the cylindrical tube forming a barrel portion of the pistol-shaped housing.

* * * * *

UNITED STATES PATENT AND TRADEMARK OFFICE
CERTIFICATE OF CORRECTION

PATENT NO. : 4,282,867

DATED : August 11, 1981

INVENTOR(S) : Rudolph M. Du Toit

It is certified that error appears in the above-identified patent and that said Letters Patent is hereby corrected as shown below:

On the title page, assignees should read

-- (73) Assignees: Hans Rudolf Kabutz and Christopher Edward Frank Corker, both of South Africa --.

Signed and Sealed this

Fifth Day of July 1983

[SEAL]

Attest:

GERALD J. MOSSINGHOFF

Attesting Officer

Commissioner of Patents and Trademarks